United States Patent [19]

Niemers et al.

[11] Patent Number: 4,567,188
[45] Date of Patent: Jan. 28, 1986

[54] HYPOTENSIVE 2-NITRO-1,1-ETHENEDIAMINES

[75] Inventors: Ekkehard Niemers; Andreas Knorr, both of Wuppertal; Bernward Garthoff, Hilden, all of Fed. Rep. of Germany

[73] Assignee: Bayer Aktiengesellschaft, Leverkusen, Fed. Rep. of Germany

[21] Appl. No.: 522,069

[22] Filed: Aug. 10, 1983

[30] Foreign Application Priority Data

Sep. 1, 1982 [DE] Fed. Rep. of Germany ....... 3232462

[51] Int. Cl.⁴ .................... C07D 213/74; C07C 87/60; A61K 31/44; A61K 31/135
[52] U.S. Cl. .................... 514/332; 514/353; 514/357; 514/655; 514/646; 546/261; 546/264; 546/296; 546/297; 546/300; 546/306; 546/332; 549/68; 549/76; 549/480; 549/495; 564/306; 564/371; 564/245; 564/246; 544/322; 544/242
[58] Field of Search ............... 546/284, 297, 283, 300, 546/261, 306, 264, 332, 296; 549/63, 475, 68, 476, 59, 480, 60, 76, 495, 472; 564/306, 245, 371, 246; 424/251, 285, 263, 326, 275, 330; 544/296, 318, 310, 326, 311, 328, 312, 331, 313, 332, 314, 333, 316, 334, 317, 335, 322, 242; 514/332, 353, 357, 655, 646

[56] References Cited

U.S. PATENT DOCUMENTS 4,247,558 1/1981 Durant et al. .................... 546/332

OTHER PUBLICATIONS

Petersen, H. J., "N-Substituted N''-Cyano-N'-Pyridyl-guanidine Derivatives" Chemical Abstracts 85:142993e (1976).

Arrigoni-Martelli, E. et al., "N''-Cyano-N-4-Pyridyl-N'-1,2,2-Trimethylpropylguanidine, Monohydrate" Chemical Abstracts 93:19242x (1980).

Primary Examiner—Henry R. Jiles
Attorney, Agent, or Firm—Sprung Horn Kramer & Woods

[57] ABSTRACT

Compounds of the formula

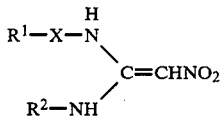

in which
R¹ is an optionally substituted aryl or heteroaryl radical,
R² is an alkyl or alkenyl radical which is optionally substituted by alkoxy or cycloalkyl, or an optionally substituted aryl or heteroaryl radical, and X is an optionally aklyl-substituted methylene radical or a direct bond, but if X is a direct bond R² is not aryl, or physiologically acceptable acid addition salts thereof, exhibit activity on the circulation system particularly as hypotensive agents.

10 Claims, No Drawings

HYPOTENSIVE 2-NITRO-1,1-ETHENEDIAMINES

The present invention relates to new 2-nitro-1,1-ethenediamines, several processes for their preparation and their use as medicaments which influence the circulation, in particular as hypotensive agents.

It has already been disclosed that 2-nitro-1,1-ethenediamines are obtained when 1-nitro-2,2-bismethylthioethene is reacted with amines (R. Gompper and H. Schaefer, Chem. Ber. 100, 591–604 (1967)).

It is also known that certain 2-nitro-1,1-ethenediamines have interesting pharmacological properties (British Patent Specification No. 1,564,502).

The invention relates to 2-nitro-1,1-ethenediamines of the general formula I,

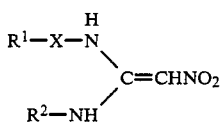
(I)

in which
  $R^1$ represents an aryl or heteroaryl radical, which is optionally substituted,
  $R^2$ represents straight-chain, branched or cyclic alkyl or alkenyl, which is optionally substituted by alkoxy or cycloalkyl, or an optionally substituted aryl or heteroaryl radical and X represents a single bond, or a methylene group, which is optionally alkyl-substituted, and $R^2$ is not aryl if X represents a single bond,
and their physiologically acceptable acid addition salts and their isomeric forms, in particular the cis- and trans-isomers.

It has been found that the 2-nitro-1,1-ethenediamines of the general formula (I) according to the invention are obtained by a process in which (a) 2-nitro-1-aminoethenes of the general formula (II)

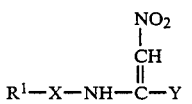
(II)

in which
Y represents alkylmercapto or alkylsulphinyl and
$R^1$ and X have the abovementioned meaning,
are reacted with amines of the general formula (III)

(III)

in which
$R^2$ has the abovementioned meaning,
or (b) 2-nitro-1-aminoethenes of the general formula (IV)

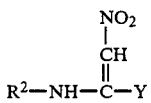
(IV)

in which
$R^2$ and Y have the abovementioned meaning, are reacted with amines of the general formula (V)

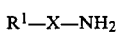
(V)

in which
$R^1$ and X have the abovementioned meaning, if appropriate in the presence of inert organic solvents, at temperatures between 0° and 180° C.

If 2-nitro-1,1-anilino-1-methylthioethene and 1,2,2-trimethylpropylamine are used as starting substances, the course of the reaction can be represented by the following equation:

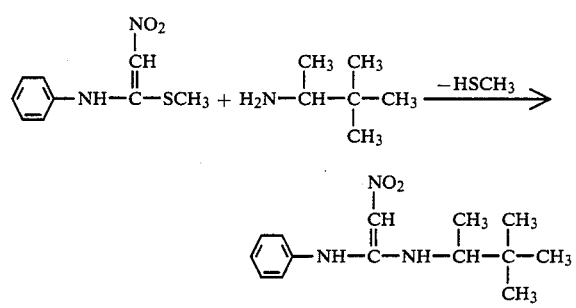

2-Nitro-1-aminoethenes of the formulae (II) and (IV) used as the starting material from the literature and can be prepared by known processes (compare Chem. Ber. 100, 591–604 (1967) and Belgian Patent Specification No. 841,526).

Amines of the general formulae (III) and (V) are likewise known, and can be prepared by known methods (compare Houben-Weyl XI/1 (1957)).

All the inert organic solvents are suitable as diluents in the process for the preparation of the new 2-nitro-1,1-ethenediamines. Preferred solvents include hydrocarbons, such as hexane, toluene and xylene, chlorinated hydrocarbons, such as methylene chloride, chloroform and chlorobenzene, ethers, such as diethyl ether, dioxane and tetrahydrofuran, alcohols, pyridine, dimethylsulphoxide, dimethylformamide and acetic acid. However, it is occasionally advantageous not to use a solvent. The reaction temperatures can be varied within a substantial range. In general, the reaction is carried out between about 0° C. and about 180° C., preferably between 20° C. and 140° C. The reaction can be carried out under normal pressure or under increased pressure.

In carrying out the process according to the invention, 1 to 5 mols of amine are preferably employed per mol of 2-nitro-1-aminoethene.

It is occasionally advantageous to add catalytic amounts of an acid, such as, for example, p-toluenesulphonic acid or acetic acid.

Unless indicated otherwise, alkyl in the present application denotes straight-chain or branched alkyl with 1 to 8 carbon atoms, in particular with 1 to 4 carbon atoms. In the definition of the substituent $R^2$ in the general formulae (I), (III) and (IV), alkyl preferably represents straight-chain or branched alkyl with 1 to 10, in particular 3 to 8, carbon atoms.

Examples which may be mentioned are n- and i-propyl, n-, i- and t-butyl, 1,1-dimethylpropyl, 2,2-dimethylpropyl, n-pentyl, 1,2,2-trimethylpropyl, 1,1-dimethylbutyl, 1,1,2-trimethylpropyl, 1-ethyl-1-methylpropyl, n-hexyl, 1,1,3-trimethylbutyl, 1,1-diethylpropyl, n-heptyl and n-octyl.

Optionally substituted aryl in the definition of $R^1$ and $R^2$ is aryl with preferably 6 to 10 carbon atoms in the aryl part, in particular phenyl or naphthyl. The aryl radicals can be mono-, di- or tri-substituted by the following substituents: halogen, alkyl, alkoxy and alkylmercapto with in each case 1–4 C atoms, trifluoromethyl, nitro, cyano, hydroxyl, amino, alkylamino and dialkylamino.

Optionally substituted hetaryl in the definition of $R^1$ and $R^2$ is preferably 2-thienyl, 3-thienyl, 2-furyl, 3-furyl, 2-pyridyl, 3-pyridyl, 4-pyridyl, 2-pyrimidyl, 4-pyrimidyl or 5-pyrimidyl. These radicals can be mono- or di-substituted by alkyl, alkoxy with 1 to 4 C atoms, hydroxyl or halogen.

In the general formulae I, II and V, X represents, inter alia, a methylene bridge, which can be mono- or di-substituted by alkyl radicals. These alkyl radicals can be straight-chain or branched and preferably contain 1 to 10, in particular 1 to 4, carbon atoms.

Compounds of the general formula (I) according to the invention which are of particular interest are those in which $R^1$ represents phenyl, which is optionally mono-, di- or tri-substituted by identical or different substituents from the group comprising halogen, trifluoromethyl and alkyl, alkoxy and alkylmercapto with in each case 1 to 4 carbon atoms, or represents pyridyl or pyrimidyl, $R^2$ represents phenyl, which is optionally mono- or di-substituted by identical or different substituents from the group comprising halogen, trifluoromethyl and alkyl and alkoxy with in each case 1 to 4 carbon atoms, or represents straight-chain, branched or cyclic alkyl with 1 to 8 carbon atoms, or represents straight-chain, branched or cyclic $C_3$–$C_8$-alkenyl, which is optionally substituted by alkoxy with 1 to 4 carbon atoms or by $C_3$–$C_7$-cycloalkyl, and X represents a methylene group or a single bond, and their physiologically acceptable acid addition salts.

The new compounds have a broad and diverse pharmacological action spectrum and a surprisingly long duration of action.

In detail, it was possible to demonstrate the following main actions in animal experiments:
1. The tone of the smooth muscle of the vessels is greatly reduced under the action of the compounds. This vascular spasmolytic action can take place in the entire vascular system, or can manifest itself more or less isolated in circumscribed vascular regions (such as, for example, the central nervous system). The compounds are therefore particularly suitable as cerebral therapeutics.
2. The compounds lower the blood pressure of normotonic and hypertonic animals and can thus be used as antihypertensive agents.

On the basis of these properties, the compounds according to the invention are suitable for the prophylaxis of acute and chronic ischaemic heart disease in the broadest sense, for the therapy of high blood pressure and for the treatment of disorders in cerebral and peripheral blood flow.

The new active compounds can be converted in a known manner into the customary formulations, such as tablets, capsules, dragees, pills, granules, aerosols, syrups, emulsions, suspensions and solutions, using inert non-toxic, pharmaceutically suitable excipients or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silica and silicates) and sugars (for example raw sugar, lactose and glucose), emulsifiers, (for example polyoxyethylene fatty acid esters, polyoxyethylene fatty alcohol ethers, alkylsulphonates and arylsulphonates), dispersing agents (for example, lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, especially perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be co-used when making tablets. In the case of aqueous suspensions and/or elixirs which are intended for oral use, the active compounds can be mixed with various flavor-improving agents or colorants in addition to the abovementioned auxiliary substances.

In the case of parenteral use, solutions of the active compounds, employing suitable liquid excipients, can be used.

In general, it has proved advantageous, in the case of intravenous administration, to administer amounts of about 0.001 to 10 mg/kg, preferably about 0.05 to 5 mg/kg, of body weight daily to achieve effective results, and in the case of oral administration, the dosage is about 0.05 to 20 mg/kg, preferably 0.5 to 5 mg/kg, of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and the nature of the formulation of the medicament and the time or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. The above statements apply in the general sense in this case also.

EXAMPLE 1

2-Nitro-1-anilino-1-(1,2,2-trimethylpropylamino)-ethene

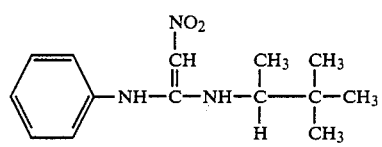

A mixture of 10.5 g (0.05 mol) of 2-nitro-1-anilino-1-methylthioethene and 15.2 g (0.15 mol) of 1,2,2-trimethylpropylamine was heated at 100° C. for 5 hours. After the mixture had cooled, it was concentrated on a rotary evaporator and the residue was recrystallized from ethanol.

Melting point: 200°–202° C. Yield: 9.1 g (69% of theory).

The following compounds were also prepared by the process described in Example 1:

| Example | R¹ | X | R² | Melting point |
|---|---|---|---|---|
| 2 | 2-pyridyl | CH₂ | phenyl | 176° |
| 3 | 3-pyridyl | CH₂ | phenyl | 213° |
| 4 | 4-pyridyl | CH₂ | —CH(CH₃)—C(CH₃)₂—CH₃ | 185° |
| 5 | 3-pyridyl | CH₂ | —CH(CH₃)—C(CH₃)₂—CH₃ | 189° |
| 6 | 2,6-dimethylphenyl | — | cyclohexyl | 241° |
| 7 | phenyl | — | cyclohexyl | 191° |
| 8 | phenyl | — | n-C₆H₁₃ | 166° |
| 9 | 2,4,6-trimethylphenyl (CH₃ at 2,4,6) | — | n-C₆H₁₃ | 165° |
| 10 | phenyl | CH₂ | 4-OC₂H₅-phenyl | 222° |
| 11 | 4-pyridyl | CH₂ | 4-OC₂H₅-phenyl | 201° |
| 12 | 4-pyridyl | CH₂ | phenyl | 207° |
| 13 | 4-pyridyl | CH₂ | 2,3-dimethylphenyl | 194° |
| 14 | 2,3-dimethylphenyl | — | cyclohexyl | 162° |
| 15 | 4-chloro-2-methylphenyl | — | n-C₆H₁₃ | 126° |
| 16 | 2,6-dimethylphenyl | — | n-C₆H₁₃ | 152° |
| 17 | 2-pyridyl | CH₂ | 2,6-dimethylphenyl | 189° |
| 18 | 2-pyridyl | CH₂ | phenyl | 176° |
| 19 | 3-pyridyl | CH₂ | phenyl | 213° |

-continued

| Example | R¹ | X | R² | Melting point |
|---|---|---|---|---|
| 20 | 2-pyridyl | CH₂ | 4-OCH₃-phenyl | 172° |
| 21 | 2-pyridyl | CH₂ | 3,4-di-OCH₃-phenyl | 166° |
| 22 | 2-pyridyl | CH₂ | 4-OC₂H₅-phenyl | 183° |
| 23 | phenyl | — | —CH₂—CH₂—OCH₃ | 158° |
| 24 | 2,6-dimethylphenyl | — | —CH₂—CH₂—OCH₃ | 167° |
| 25 | 2-pyridyl | CH₂ | 2,3-dimethylphenyl | 174° |
| 26 | 2,3-dimethylphenyl | — | —CH₂—CH₂—OCH₃ | 174° |
| 27 | 2-Cl-4-H₃CS-phenyl | CH₂ | 4-OC₂H₅-phenyl | — |
| 28 | 2-Cl-4-H₃CS-phenyl | — | cyclohexyl | 176° |
| 29 | 2-Cl-4-H₃CS-phenyl | — | —CH₂—CH₂—OCH₃ | 218° |
| 30 | 2-pyridyl | CH₂ | 3-Cl-4-OCH₃-phenyl | 197° |
| 31 | phenyl | CH₂ | 2,3-dimethylphenyl | 186° |
| 32 | 2-Cl-4-H₃CO-phenyl | — | cyclohexyl | 189° |
| 33 | 2-OC₂H₅-phenyl | — | —CH(CH₃)—C(CH₃)₂—CH₃ | 197° |
| 34 | 2-OCH₃-phenyl | — | —CH(CH₃)—C(CH₃)₂—CH₃ | 205° |
| 35 | 2-OC₂H₅-phenyl | — | —C(CH₃)₃ | |
| 36 | phenyl | — | —CH₂—C(CH₃)₃ | 197° |
| 37 | phenyl | — | —CH₂—CH(C₂H₅)₂ | |
| 38 | 2-pyridyl | — | —CH(CH₃)—C(CH₃)₂—CH₃ | |
| 39 | 3-pyridyl | — | —CH(CH₃)—C(CH₃)₂—CH₃ | 182° C. |
| 40 | 4-pyridyl | — | —CH(CH₃)—C(CH₃)₂—CH₃ | 110° C. |
| 41 | 4-HO-phenyl | — | —CH(CH₃)—C(CH₃)₂—CH₃ | 243° |

-continued

| Example | R¹ | X | R² | Melting point |
|---|---|---|---|---|
| 42 | H₃CO-⟨phenyl⟩- | — | -CH(CH₃)-C(CH₃)₂-CH₃ | 229° |
| 43 | H₃CO-⟨phenyl with OCH₃⟩- | — | -CH(CH₃)-C(CH₃)₂-CH₃ | 233° |
| 44 | H₅C₂O-⟨phenyl⟩- | — | -CH(CH₃)-C(CH₃)₂-CH₃ | 207° |
| 45 | H₃CO-⟨phenyl⟩- | — | -CH(CH₃)-C(CH₃)₂-CH₃ | 168° |
| 46 | H₅C₂O-⟨phenyl⟩- | — | -CH(CH₃)-C(CH₃)₂-CH₃ | 164° |
| 47 | CH₃,CH₃-⟨phenyl⟩- | — | -CH(CH₃)-C(CH₃)₂-CH₃ | 236° |

It will be understood that the specification and examples are illustrative but not limitative of the present invention and that other embodiments within the spirit and scope of the invention will suggest themselves to those skilled in the art.

What is claimed is:

1. A compound of the formula

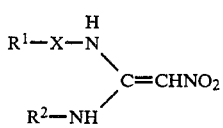

in which
R¹ is aryl with 6 to 10 carbon atoms optionally substituted up to three times by halogen, lower alkyl, lower alkoxy, trifluoromethyl, methylmercapto, nitro and/or cyano or is pyridyl optionally substituted by lower alkyl or halogen,
R² is alkyl with 1 to 10 carbon atoms optionally substituted by lower alkoxy or independently is any of the radicals of R¹, and
X is methylene radical optionally substituted by lower alkyl, or a direct bond but if X is a direct bond R² is not aryl,
or a physiologically acceptable acid addition salt thereof.

2. A compound according to claim 1, wherein such compound is 2-nitro-1-anilino-1-(1,2,2-trimethylpropylamino)-ethane of the formula

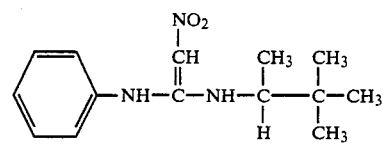

or a physiologically acceptable acid addition salt thereof.

3. A compound according to claim 1, wherein such compound is 2-nitro-1-(2-ethoxyanilino)-1-(1,2,2-trimethylpropylamino)-ethane of the formula

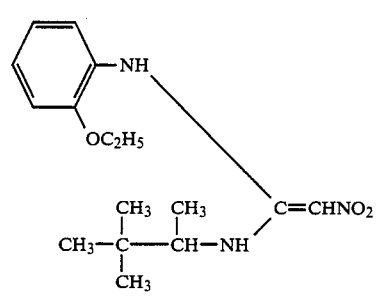

or a physiologically acceptable acid addition salt thereof.

4. A compound or salt according to claim 1, wherein such compound is 2-nitro-1-(2-methoxyanilino)-1-(1,2,2-trimethylpropylamino)-ethane of the formula

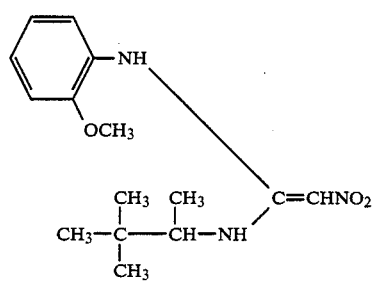

or a physiologically acceptable acid addition salt thereof.

5. A compound according to claim 1, wherein such compound is 2-nitro-1-(pyrid-3-ylamino)-1-(1,2,2-trimethylpropylamino)-ethane of the formula

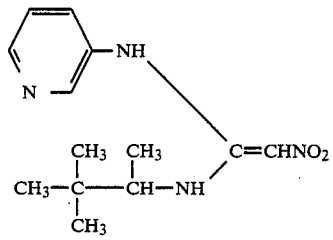

or a physiologically acceptable acid addition salt thereof.

6. A compound according to claim 1, wherein such compound is 2-nitro-1-(2,6-dimethylanilino)-1-(1,2,2-trimethylpropylamino)-ethane of the formula

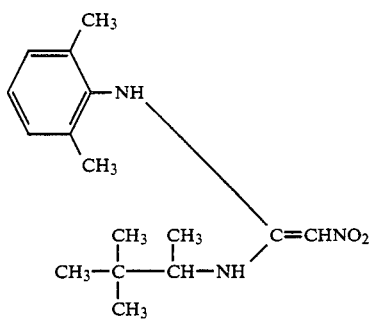

or a physiologically acceptable acid addition salt thereof.

7. A composition for treating acute and chronic ischemic heart disease, for reducing high blood pressure or for treating disorders in cerebral and peripheral blood flow in which a hypotensive agent would be useful, comprising an amount effective therefor of a compound or salt according to claim 1 in admixture with a pharmaceutically acceptable diluent.

8. A composition according to claim 7 in the form of a pill, capsule or tablet containing a unit dose.

9. A method of treating acute and chronic ischemic heart disease, of reducing high blood pressure or of treating disorders in cerebral and peripheral blood flow in which a hypotensive agent would be useful, comprising administering to a patient suffering therefrom an amount effective therefor of a compound or salt according to claim 1.

10. The method according to claim 9, wherein such compound is
2-nitro-1-anilino-1-(1,2,2-trimethylpropylamino)-ethane,
2-nitro-1-(2-ethoxyanilino)-1-(1,2,2-trimethylpropylamino)-ethane,
2-nitro-1-(2-methoxyanilino)-1-(1,2,2-trimethylpropylamino)-ethane,
2-nitro-1-(pyrid-3-ylamino)-1-(1,2,2-trimethylpropylamino)-ethane, or
2-nitro-1-(2,6-dimethylanilino)-1-(1,2,2-trimethylpropylamino)-ethane,
or a physiologically acceptable acid addition salt thereof.

* * * * *